United States Patent [19]

Curran

[11] 4,092,320

[45] May 30, 1978

[54] CERTAIN 1-(N-ACYL)-CARBOTHIOAMIDES OF 1,5-NAPHTHYRIDINE DERIVATIVES

[75] Inventor: Adrian Charles Ward Curran, South Cave, England

[73] Assignee: John Wyeth & Brother Limited, Maidenhead, England

[21] Appl. No.: 785,636

[22] Filed: Apr. 7, 1977

Related U.S. Application Data

[63] Continuation-in-part of Ser. No. 676,034, Apr. 12, 1976, abandoned, which is a continuation-in-part of Ser. No. 553,964, Feb. 29, 1975, Pat. No. 3,960,876.

[30] Foreign Application Priority Data

Mar. 5, 1974  United Kingdom ................. 9764/74
Jul. 12, 1974  United Kingdom ............... 30935/74

[51] Int. Cl.$^2$ ........................................... C07D 471/04
[52] U.S. Cl. ............................. 260/294.8 C; 424/256
[58] Field of Search .................................. 260/294.8 C

[56] References Cited

U.S. PATENT DOCUMENTS 3,149,104  9/1964  Lesher et al. ..................... 260/295 N
3,745,162  7/1973  Heisley ............................. 260/283 D Primary Examiner—Alan L. Rotman
Attorney, Agent, or Firm—Arthur E. Wilfond

[57] ABSTRACT

The invention relates to N-acyl thioureas which are derivatives of 1,5-Naphthyridines. The compounds are intermediates for anti-ulcer agents.

4 Claims, No Drawings

CERTAIN 1-(N-ACYL)-CARBOTHIOAMIDES OF 1,5-NAPHTHYRIDINE DERIVATIVES

This application is a continuation-in-part of my application U.S. Ser. No. 676,034, filed Apr. 12, 1976, now abandoned, which in turn is a continuation-in-part of my application U.S. Ser. No. 553,964, filed Feb. 29, 1975 now U.S. Pat. No. 3,960,876.

The invention relates to novel organic compounds, and to processes for preparing them.

According to the invention there is provided compounds of formula (I)

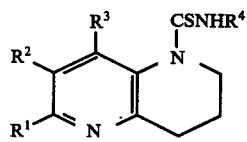

and pharmaceutically acceptable acid addition salts thereof wherein $R^1$, $R^2$ and $R^3$ are the same or different and represent a hydrogen atom or lower alkyl of 1–6 carbon atoms which may be substituted by lower alkoxy of 1–6 carbon atoms and $R^4$ is lower alkanoyl or aroyl.

When any of $R^1$, $R^2$ or $R^3$ is a lower alkyl radical then this may be a straight or branched chain, having from 1 to 6 carbon atoms, e.g. methyl, ethyl, n-, and isopropyl and n-, s- and t-butyl. The term alkyl radical is also intended to embrace cyclic alkyl radicals e.g. cyclobutyl, cyclopentyl and cyclohexyl.

The term "lower alkoxy" as used in this specification means alkoxy radicals having from 1 to 6 carbon atoms e.g. methoxy, ethoxy, propoxy, butoxy, pentoxy and hexoxy.

Preferably when $R^1$ and $R^2$ or $R^2$ and $R^3$ are both alkyl, they are selected from normal and secondary alkyl groups. More preferred $R^1$, $R^2$ and $R^3$ are selected from hydrogen and methyl. Particularly preferred compounds are those in which at least one of $R^1$, $R^2$ and $R^3$ is methyl and the others are hydrogen.

The group $R^4$ may be aroyl or lower alkanoyl.

Examples of aroyl groups are benzoyl and substituted benzoyl e.g. halobenzoyl, such as chlorobenzoyl. The lower alkanoyl group is one having from 2 to 7 carbon atoms e.g. acetyl, propionyl, butyryl, pentanoyl and hexanoyl.

Compounds of formula I wherein $R^4$ is lower alkanoyl or aroyl are intermediates for corresponding compounds of formula I where $R^4$ is hydrogen. These compounds are anti-ulcer agents, which are active in one or more of the following pharmacological tests namely anti-ulcer, anti-secretory or gastric anti-histamine activity. Activity in one of these three tests denotes an anti-ulcer agent.

The invention includes processes for preparing the compounds of formula I.

A process for preparing compounds of formula I wherein $R^4$ is lower alkanoyl or aroyl comprises reacting a compound of formula II (II)

with an isothiocyanate of formula $R^4NCS$ wherein $R^4$ is lower alkanoyl or aroyl, and $R^1$, $R^2$ and $R^3$ are as defined above.

Compounds of formula I, wherein $R^4$ is hydrogen may be prepared by hydrolysing a compound of formula I wherein $R^4$ is lower alkanoyl or aroyl.

The hydrolysis may be carried out by treatment with a suitable base e.g. an alkali or alkaline earth metal hydroxide. Conveniently sodium or potassium hydroxide may be used. Alternatively acid hydrolysis may be employed.

The compounds of formula I can form acid addition salts with inorganic acids e.g. hydrochloric, hydrobromic, sulphuric or nitric acids, or organic acids e.g. citric, fumaric, maleic or tartaric acids. These acid addition salts are included in the invention.

As stated above the active compounds of formula I, wherein $R^4$ is hydrogen, (produced by hydrolysis of compounds of formula I where $R^4$ is lower alkanoyl or aroyl) are anti-ulcer agents which display activity in tests for one or more of the following: anti-ulcer, anti-secretory or gastric anti-histamine activity. Anti-ulcer activity is determined by the method of Brodie and Hanson, J. Applied Physiology, 15, 291, 1960.

Anti-secretory activity and gastric antihistamine activity are determined by the method of H. Shay, D. Sun and H. Greenstein, Gastroenterology 1954, 26, 906–13.

The starting compounds of formula II are described in the literature or may be made by methods analogous to those described in the literature. A convenient method is reduction of the corresponding 1,5-naphthyridine as described in Advances in Heterocyclic Chemistry 11, 1970 at pages 158–161. The 1,5-naphthyridines may be prepared as described in the same article at pages 136–140.

Thus 3-amino pyridine III may be condensed with a glycerol of formula IV to give the

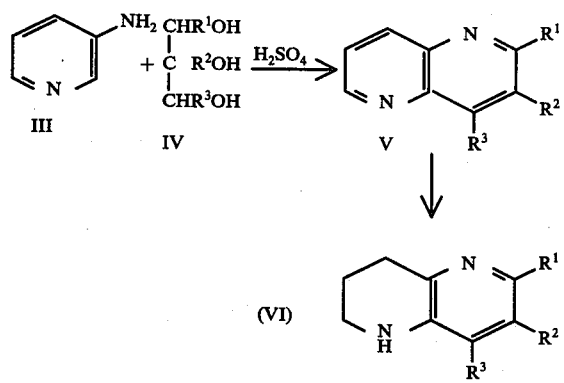

1,5-naphthyridine of formula V which is reduced e.g. by hydrogenation over platinum oxide to the 1,2,3,4-tetrahydro-1,5,-naphthyridine of formula (VI). In formula IV, V and VI $R^1$, $R^2$ and $R^3$ are as defined in connection with formula I.

If $R^1$ and $R^3$ are different in formula (IV) then a mixture of products of formula V (in which $R^1$ or $R^3$ is adjacent to the nitrogen atom) may be formed which can be separated by standard methods e.g. gas liquid chromatography.

Alternatively a substituted pyridine of formula IIIa

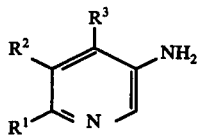

may be reacted with

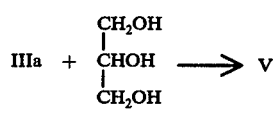

glycerol to give compound V which is then reduced to compound (VI). This route is useful when $R^1$ and $R^3$ are different.

The invention is illustrated by the following examples. Temperatures are in ° C.

EXAMPLE 1

1,2,3,4-Tetrahydro-1-(N-benzoylthiocarboxamido)-1,5-naphthyridine 1,5-Naphthyridine was prepared from 3-aminopyridine according to the method described in J. Org. Chem., 1963, 1757 and was isolated as colourless needles from n-hexane m.p. 69° C (lit. 74°). 1,5-Naphthyridine (2.6 g.) was hydrogenated in 95% ethanol over $PtO_2$ catalyst under atmospheric conditions to give 1,2,3,4-tetrahydro-1,5-naphthyridine as colourless needles (2.51 g.).

A solution of 1,2,3,4-tetrahydro-1,5-naphthyridine (2.68g, 0.02 mole) prepared as described above, in acetonitrile (20 ml) was treated dropwise with stirring with a solution of benzoyl isothiocyanate (3.62g, 0.02mole) in acetonitrile (5ml). After ¼ hour the precipitate was removed by filtration and washed with acetonitrile to give 1,2,3,4-tetrahydro-1,5-naphthyridine-1-(N-benzoyl)thiocarboxamide (5.2g, 88%) m.p. 177–9° decomp. (Found: C, 64.5; H, 5.2; N, 14.5. $C_{16}H_{15}N_3OS$ requires C, 64.6; H, 5.1; N, 14.1%).

The product may be hydrolysed to give 1,2,3,4-tetrahydro-1-(thiocarboxamido)-1,5-naphthyridine.

EXAMPLE 2

1-(N-p-Chlorobenzoylthiocarboxamido)-1,2,3,4-tetrahydro-1,5-naphthyridine 1,2,3,4-Tetrahydro-1,5-naphthyridine is treated with p-chlorobenzoyl isothiocyanate according to the method of Example 1 to give the title compound which may be hydrolysed with 10% sodium hydroxide to give 1,2,3,4-tetrahydro-1,5-naphthyridine-1-thiocarboxamide.

EXAMPLE 3

1-(N-acetylthiocarboxamido)-1,2,3,4-tetrahydro-1,5-naphthyridine 1,2,3,4-tetrahydro-1,5-naphthyridine is treated with acetyl isothiocyanate according to the method of Example 1 to give the title compound.

EXAMPLE 4

1-(N-acetylthiocarboxamido)-6-methyl-1,2,3,4-tetrahydro-1,5-naphthyridine

2-Methyl-5,6,7,8-tetrahydronaphthyridine is treated with acetyl isothiocyanate following the procedure of Example 1 to obtain the title compound. (In the product the 5-nitrogen atom of the starting material is renumbered 1 and the 2-methyl substituent of the starting material is renumbered 6.)

EXAMPLE 5

1-(N-benzoylthiocarboxamido)-8-methyl-1,2,3,4-tetrahydro-1,5-naphthyridine

4-Methyl-5,6,7,8-tetrahydro-1,5-naphthyridine is treated with benzoyl isothiocyanate according to the procedure of Example 1 to obtain the title compound. (In the product the 5-nitrogen atom of the starting compound is renumbered 1 and the 4-methyl substituent is renumbered 8).

EXAMPLE 6

1-(N-acetylthiocarboxamido)-6,8-dimethyl-1,2,3,4-tetrahydro-1,5-naphthyridine 2,4-Dimethyl-5,6,7,8-tetrahydro-1,5-naphthyridine is treated with acetyl isothiocyanate following the procedure of Example 1 to give the title compound. (In the product the 5-nitrogen atom of the starting compound is renumbered 1 and the 2,4-methyl substituents are renumbered 6,8).

I claim:
1. A compound of formula (I)

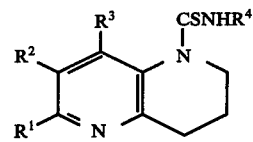

or a pharmaceutically acceptable acid addition salt thereof wherein $R^1$, $R^2$ and $R^3$ are the same or different and represent a hydrogen atom or lower alkyl of 1–6 carbon atoms which may be substituted by lower alkoxy of 1–6 carbon atoms, and $R^4$ is benzoyl or halobenzoyl with the proviso that when $R^1$ and $R^2$ or $R^2$ and $R^3$ are both alkyl they are selected from normal or secondary alkyl groups.

2. A compound of formula (I)

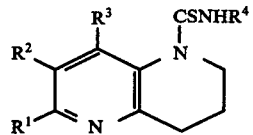

wherein $R^1$, $R^2$ and $R^3$ are individually selected from hydrogen and methyl and $R^4$ is benzoyl or halobenzoyl.

3. The compound of claim 2, wherein $R^1$, $R^2$ and $R^3$ are selected from hydrogen and methyl and $R^4$ is benzoyl.

4. A compound of claim 2, which is 1,2,3,4-tetrahydro-1,5-naphthyridine-1-(N-benzoyl)thiocarboxamide.

* * * * *